(12) United States Patent
Simon

(10) Patent No.: US 6,333,053 B1
(45) Date of Patent: Dec. 25, 2001

(54) USE OF A SPECIFIC PARTICULATE PHASE IN A COSMETIC COMPOSITION, IN PARTICULAR A MAKEUP COMPOSITION, AND COSMETIC COMPOSITION COMPRISING SUCH A PARTICULATE PHASE

(75) Inventor: Jean-Christophe Simon, Paris (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 09/411,384

(22) Filed: Oct. 4, 1999

(30) Foreign Application Priority Data

Oct. 6, 1998 (FR) .................................. 98 12502

(51) Int. Cl.$^7$ ...................................... A61K 9/14

(52) U.S. Cl. ............... 424/489; 424/63; 424/69; 424/70.7; 424/401

(58) Field of Search ............... 424/63, 64, 70.7, 424/489, 407

(56) References Cited

U.S. PATENT DOCUMENTS

| | | | |
|---|---|---|---|
| 4,906,070 | 3/1990 | Cobb, Jr. ............... | 359/831 |
| 5,056,892 | 10/1991 | Cobb ............... | 350/286 |
| 5,082,660 | 1/1992 | Ounanian et al. ............... | 424/63 |
| 5,223,559 | * 6/1993 | Arraudeau et al. ............... | 524/47 |
| 5,288,481 | 2/1994 | Ounanian et al. ............... | 424/63 |
| 5,320,834 | 6/1994 | Ounanian et al. ............... | 424/63 |
| 5,858,381 | 1/1999 | Le Bras ............... | 424/401 |
| 5,866,108 | 2/1999 | Le Bras ............... | 424/63 |

FOREIGN PATENT DOCUMENTS 0 651 991 A1  5/1995  (EP) .
2 673 372  9/1992  (FR) .

OTHER PUBLICATIONS

"3M Brightness Enhancement Film (BEF) II, 3M Electronic Display Lighting", Circular Nos. 75–0500–1690–8 (1997).
3M Brightness Enhancement Film (BEF) II, 3M Electronic Display Lighting, Circular Nos. 75–0500–2361–1 (1997).
Thurn–Müller et al., "Transparent Colors", Seifen–Öle–Fette–Wachse vol. 117, No. 20, Dec. 12, 1991, No. 20, pp. 775–778.
JP 08059436–A, Mar. 5, 1996, Cosmetic material having no gelling, sedimentation, etc., Chemical Abstract.
KR 9101305–B, May 18, 1991, Cosmetic composition for manufacturing of emulsion–type makeup foundation, Chemical Abstract.
KR 9103103–B, May 18, 1991, Cosmetic composition preparation, Chemical Abstract.

(List continued on next page.)

Primary Examiner—Shelley A. Dodson
Assistant Examiner—Konata M. George
(74) Attorney, Agent, or Firm—Nixon & Vanderhye P.C.

(57) ABSTRACT

Use of a specific particulate phase in a cosmetic composition, in particular a make-up composition, and cosmetic composition comprising such a particulate phase. Use of a particulate phase comprising particles with mean dimensions ranging from 5 to 100 microns and preferably from 20 to 50 microns and comprising at least two consecutive faces, the normals of which at the median point form, between one another, an angle at least equal to 90°, in a cosmetic composition, in particular a make-up composition, for the purpose of limiting, decreasing or eliminating the blemishes of keratinous substances and/or of modifying the perception of the volume of some regions of the said substances.

Cosmetic composition, in particular in make-up composition, such as a foundation, comprising such a particulate phase.

47 Claims, 1 Drawing Sheet

OTHER PUBLICATIONS

KR 9103076–B, May 18, 1991, Make–up cosmetic composition, Chemical Abstract.

KR 9103074–B, May 18, 1991, Cosmetic powder preparation, Chemical Abstract.

JP 55–7212, Jan. 8, 1980, Cosmetic Chemical Abstract.

JP 63–225666, Sep. 20, 1988, Monoazo Lake Pigment, Chemical Abstract.

JP 60–87317, May 17, 1985, Display Element, Chemical Abstract.

JP 59–204052, Nov. 19, 1984, Image Form Method, Chemical Abstract.

J58120673–A, Jul. 18, 1983; JP J88058189–B Nov. 15, 1988, Stable dioxazine violet dye manufacture, Chemical Abstract.

J57031965–A Feb. 20, 1980; JP J86048549–B, Oct. 24, 1986, Reddish copper phthalocyanine pigment preparation, Chemical Abstract.

\* cited by examiner

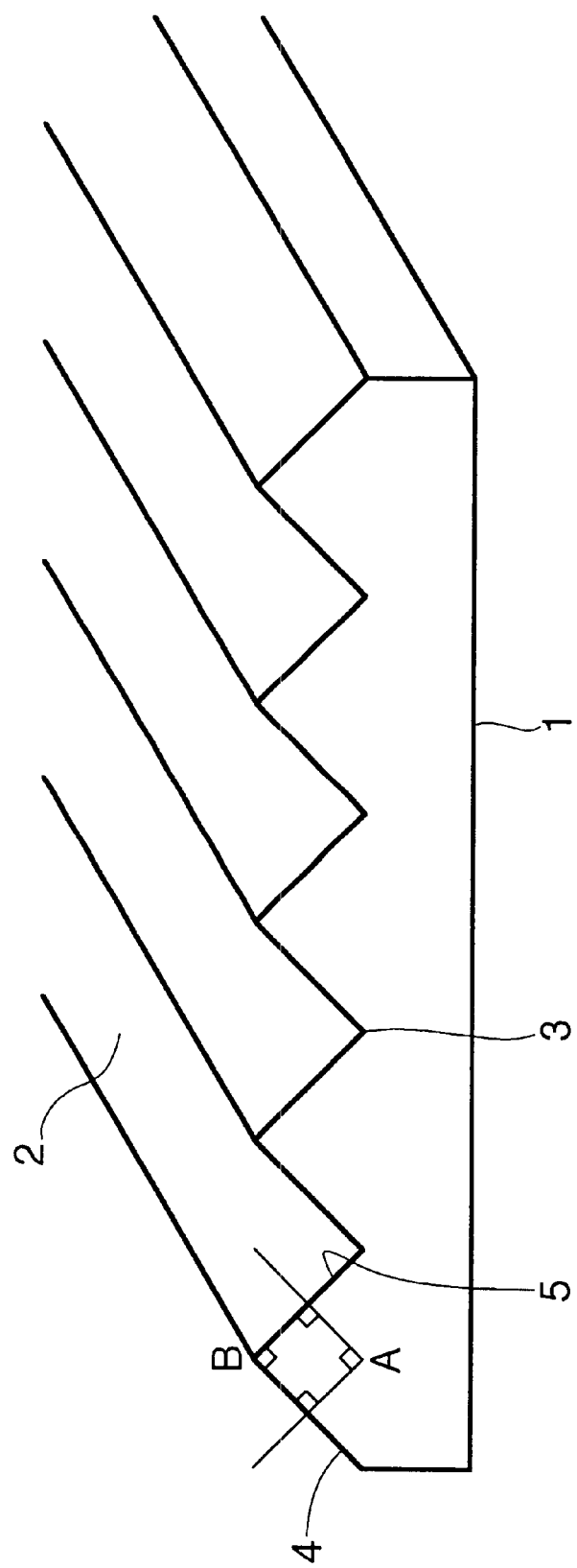

USE OF A SPECIFIC PARTICULATE PHASE IN A COSMETIC COMPOSITION, IN PARTICULAR A MAKEUP COMPOSITION, AND COSMETIC COMPOSITION COMPRISING SUCH A PARTICULATE PHASE

The subject-matter of the present invention is the use of a specific particulate phase in a cosmetic composition, in particular a make-up composition, for the purpose of limiting, decreasing or eliminating blemishes of keratinous substances, in particular the skin, and/or of remodelling the contours thereof, as well as a cosmetic composition, in particular a make-up composition, comprising such a particulate phase.

For a long time, there has been a search for fillers and/or pigments which contribute a soft focus effect, in order to give the skin a uniform appearance and to hide the imperfections thereof, such as the wrinkles or streaks which appear on the lips when a lipstick is applied. These fillers and/or pigments often have complex multilayer architectures, such as those disclosed in Patents KR 91 03105-B, KR 91 03103-B, KR 91 03076-B and KR 91 03074-B, or are particles with a spherical shape, such as those disclosed in Patent FR-A-2,673,372 or in U.S. Pat. Nos. 5,082,660, 5,288,481 and 5,320,834. These fillers of the prior art, when they are in the lamellar form or in the form of platelets, have a significant covering power which gives the skin an unnatural appearance. As regards the fillers with a spherical shape, they have a weak scattering effect, resulting in insufficient masking of the imperfections, which implies the need to use them at a high concentration, resulting in the risk of a dry and not very comfortable product.

The inventors have discovered, surprisingly, a novel type of particulate phase which makes it possible, by virtue of the shape of its particles, to obtain novel optical effects, in particular to contribute a soft focus effect and thus to soften the imperfections of the skin and of other keratinous substances and/or to remodel the contours thereof.

The particles of this particulate phase are characterized in that they comprise at least two consecutive faces, the normals of which at the median point form, between one another, an angle at least equal to 90° C., and in that they have mean dimensions ranging from 5 to 100 microns.

A subject-matter of the invention is therefore the use of a particulate phase comprising particles with mean dimensions ranging from 5 to 100 microns and comprising at least two consecutive faces, the normals of which at the median point form, between one another, an angle at least equal to 90°, in a cosmetic composition, in particular a make-up composition, for the purpose of limiting, decreasing or eliminating the blemishes of kertainous substances and/or of modifying the perception of the volume of certain regions of the said substances.

According to a preferred embodiment of the invention, the particles comprise at least two nonparallel flat consecutive faces and are therefore polyhedral in shape.

The angle formed by the normals at the median point of two consecutive faces preferably has a value ranging from 90 to 175°. Thus, in the case of two nonparallel flat consecutive faces, the angle at the vertex separating the two flat faces is at most equal to 90°. It preferably varies from 5 to 90°.

The particles of the particulate phase used according to the invention have mean dimensions preferably ranging from 20 to 50 microns.

The particles of the particulate phase used according to the invention have the distinguishing feature of refracting, scattering and reflecting the incident light, funnelling it to produce optimum luminosity and novel optical effects. They make it possible, for example, to illuminate the shadows of the face in order to cause the wrinkles there to disappear or to hide the streaks which appear on the lips when a lipstick is applied. The soft focus effect obtained can also make it possible to refine or to increase the volume of certain parts of the face and the neck and, for example, to remodel the contours of the face. The particulate phase acts as filler and/or pigment.

The particles of the particulate phase used according to the invention have a refractive index of greater than 1, preferably ranging from 1.25 to 1.9 and more preferably from 1.45 to 1.55.

The nature of the particles is not a determining factor. However, the transparency is an important criterion in obtaining the desired optical properties. It can relate to a polymeric particulate phase composed, for example, of poly(ethylene terephthalate) (PET), of polyethylene, in particular high-density polyethylene (HDPE), of polypropylene, of polytetrafluoroethylene (PTFE), of polychlorotetrafluoroethylene (PCTFE), of poly(butylene terephthalate) (PBT), of polycarbonates, of polyurethanes, of polythiourethanes, of vinyl, vinylidene or styrene polymers, such as poly(vinyl or vinylidene acrylate)s, of polyacrylic and polymethacrylic polymers, of polythioacrylates and polythiomethacrylates, of transparent silicone resins, of their mixtures and copolymers and of any other biocompatible polymer conventionally used in lenses, in particular ophthalmic lenses.

The particulate phase used according to the invention can also be composed of metal oxides, such as, for example, aluminium, hafnium, silicon, titanium, tungsten, vanadium, zinc and zirconium oxides. Of course, these oxides must be cut along crystalline planes and in particular along triclinic, rhombohedral or monoclinic lattice planes but also cubic, quadratic or orthorhombic lattice planes or be obtained by crystalline growth and exhibit such lattices.

By way of example, the particulate phase used according to the invention can be obtained by milling a modified acrylic resin sheet of A4 format with the reference BEF II (Brightness Enhancement Film II), sold by the company 3M, comprising a flat face 1 and a face 2 exhibiting uniformly positioned grooves 3, such as represented in the single appended figure. In this instance, the angle A formed by the normals at two nonparallel consecutive faces 4,5 is approximately 90°. It follows that the angle at the vertex B between the faces 4 and 5 is approximately 90°.

Another subject-matter of the present invention is a cosmetic composition and in particular a make-up composition comprising the particulate phase defined above in a cosmetically acceptable vehicle.

The particulate phase is present in the cosmetic composition according to the invention in a proportion of 0.5 to 30% by weight and preferably 2 to 15% by weight with respect to the total weight of the composition.

The composition according to the invention finds a particularly advantageous application in the field of caring for and/or making up the skin of the face, neck and body, keratinous fibres, nails, mucous membranes and/or semi-mucous membranes of human beings. The term "mucous membranes" is understood to mean in particular the internal part of the lower eyelid; the term "semi-mucous membranes" is understood to mean more particularly the lips of the face. The term "keratinous fibres" is understood to mean in particular the eyelashes, eyebrows and hair.

The cosmetic compositions according to the invention can be provided in the form of a make-up product, in particular a foundation, a face powder, an eyeshadow, an eyeliner, a mascara, a concealer or a lipstick, of a care product or of an anti-sun product.

The compositions according to the invention can be provided in the fluid, gelled, semisolid, solid or supple paste form.

They can be provided in particular in the form of a simple or complex emulsion (O/W, W/O, O/W/O or W/O/W), such as a cream, a milk or a gel cream, of an aqueous gel, aqueous/alcoholic gel or anhydrous gel which is more or less solid, of a serum, of a powder, of a paste or of a solid stick, and can optionally be packaged in an aerosol and be provided in the form of a foam or spray.

The compositions of the invention can be prepared according to techniques well known to a person skilled in the art, in particular those intended for the preparation of oil-in-water (O/W) or water-in-oil (W/O) emulsions.

When it is an emulsion, the aqueous phase of the latter can comprise a nonionic vesicular dispersion prepared according to known processes (Bangham, Standish and Watkins, J. Mol. Biol., 13, 238 (1965), FR-A-2,315,991 and FR-A-2,416,008). This dispersion can be used in particular as dispersant for the oily phase.

The make-up compositions, in particular foundations, are often provided in the form of a more or less fluid cream comprising a fatty phase, an aqueous phase and a particulate phase generally composed of fillers and/or pigments.

The fatty phase of the cosmetic composition according to the invention preferably comprises at least one volatile or non-volatile silicone oil.

Mention may be made, as examples of silicone oils used in the invention, of:

cyclic volatile silicones having from 3 to 8 silicon atoms and preferably 4 to 6, such as, for example, cyclomethicones, such as cyclotetradimethylsiloxane, cyclopentadimethylsiloxane (D5) or cyclohexadimethylsiloxane (D6), and the products sold under the names: "DC Fluid 244", "DC Fluid 245", "DC Fluid 344" and "DC Fluid 345" by the company Dow Corning, as well as those sold under the names "Abil K4" by the company Goldschmidt, under the names "Silbione 70045 V2" and "Silbione Oil 70045 V5" by the company Rhône-Poulenc and under the names "Volatile Silicone 7158" and "Volatile Silicone 7207" by the company Union Carbide;

cyclocopolymers of the dimethylsiloxane/ methylalkylsiloxane type, such as "silicone FZ 3109", sold by the company Union Carbide, which is a dimethylsiloxane/ methyloctylsiloxane cyclocopolymer;

linear volatile silicones having from 2 to 9 silicon atoms, optionally comprising a pendant $C_2$–$C_{10}$ alkyl chain or a $C_2$–$C_{10}$ alkyl chain at the chain end, for example hexamethyldisiloxane, hexylheptamethyltrisiloxane and octylheptamethyltrisiloxane;

polyalkylsiloxanes comprising trimethylsilyl end groups, preferably those for which the viscosity at 25° C. is less than or equal to 0.06 $m^2$/s, among which may be mentioned linear polydimethylsiloxanes, in particular those sold under the name "Dow Corning Fluid 200" by the company Dow Corning, alkylmethylpolysiloxanes, such as cetyl dimethicone (CTFA name), and the products sold under the names "AK" by the company Wacker, "SF" by the company General Electric and "Abil" by the company Goldschmidt, such as the product "Abil 10";

phenylated silicone oils, such as phenyl trimethicones and phenyl dimethicones;

and their mixtures.

Volatile silicone oils and in particular cyclomethicones are preferred for use in the invention.

The silicone oil used according to the invention is preferably present in a proportion of at least 5% by weight and preferably of 25 to 95% by weight with respect to the total weight of the composition.

The composition according to the invention can also comprise other silicone compounds, such as silicone gums and silicone waxes.

The silicone gums which can be used in the composition of the invention can be polysiloxanes with a high molecular mass, of the order of 200,000 to 1,000,000, and with a viscosity of greater than 500,000 mPa·s. They can be used alone or as a mixture with a solvent, such as a polydimethylsiloxane or polyphenylsiloxane oil or a cyclomethicone.

The silicone waxes which can be used in the composition according to the invention can be substituted linear polysiloxanes. Mention may be made, for example, of silicone polyether waxes or alkyl or alkoxy dimethicones having from 16 to 45 carbon atoms.

The compositions according to the invention can also comprise non-silicone fatty substances, including pasty fatty substances or gums, waxes and oils of vegetable, mineral, animal or synthetic origin.

The pasty fatty compounds can be defined using at least one of the following physicochemical properties:

a viscosity of 0.1 to 40 Pa·s (1 to 400 poises), measured at 40° C. with a Contraves TV rotary viscometer equipped with an MS-r3 or MS-r4 rotor at a frequency of 60 Hz, a melting point of 25–70° C., preferably 25–55° C.

Mention may be made, as waxes which can be used in the invention, of waxes of animal origin, such as lanolin, beeswax, spermaceti or lanolin derivatives, such as lanolin alcohols, hydrogenated, hydroxylated or acetylated lanolin, fatty acids of lanolin and acetylated lanolin alcohol; waxes of vegetable origin, such as carnauba, candelilla, kapok, ouricury, rice, hydrogenated jojoba, alfa or japan wax or cork fibre or sugar cane waxes or alternatively cocoa butter; mineral waxes, for example paraffin, montan, lignite, petrolatum or petroleum waxes or microcrystalline waxes, ceresin or ozokerite; or synthetic waxes, such as polyethylene waxes, the waxes obtained by the Fischer-Tropsch synthesis and the linear esters resulting from the reaction of a saturated $C_{10}$ to $C_{40}$ carboxylic acid and of a saturated $C_{10}$ to $C_{40}$ alcohol, such as myristyl myristate. Use may also be made of calcium lanolates or stearates and hydrogenated jojoba or coconut oil.

The fatty phase can also comprise one or more hydrocarbon-comprising or fluorine-comprising oil(s).

Mention will be made, as hydrocarbon-comprising oil, of: any fluid oil (or mixture of oils) which is stable at the usual temperature of use of cosmetic, pharmaceutical or hygiene products, such as oils of vegetable or animal, mineral or synthetic origin or triglycerides of $C_{12}$ to $C_{18}$ fatty acids.

Mention may be made, among modified or unmodified oils of vegetable or animal origin, of, for example, sweet almond oil, avocado oil, castor oil, olive oil, jojoba oil, sunflower oil, wheat germ oil, sesame oil, groundnut oil, grape seed oil, soybean oil, rapeseed oil, safflower oil, coconut oil, maize oil, hazelnut oil, karite butter, palm oil, apricot kernel oil, calophyllum oil or perhydrosqualene.

Mention may be made, among oils of mineral origin, of, for example, liquid paraffin and liquid petrolatum.

Mention may in particular be made, among synthetic oils, of fatty acid esters, such as isopropyl myristate, isopropyl palmitate, 2-ethylhexyl palmitate, purcellin oil (stearyl octanoate), isononyl or isostearyl isononanoate or isopropyl lanolate, fatty acids, such as oleic, palmitic, stearic, behenic, linoleic and linolenic acids, or volatile or non-volatile isoparaffins, such as $C_8$–$C_{16}$ isoparaffins and polyisobutenes.

The composition according to the invention preferably comprises a volatile isoparaffin.

Mention may more particularly be made, as volatile isoparaffins, of isododecane, isodecane and isohexadecane, in particular those sold under the trade names "Isopar S" and "Permethyl 99".

Use may also be made of $C_{12}$ to $C_{18}$ fatty alcohols, such as oleyl alcohol, cetyl alcohol and stearyl alcohol.

In addition, the composition according to the invention can comprise one or more surface-active agents and/or an aqueous phase and/or one or more thickening agents.

The aqueous phase can include adjuvants commonly used in aqueous gels and cosmetic emulsions. In addition, the aqueous phase can comprise from 0.5% to 20% by weight, with respect to the total weight of the aqueous phase, of a lower $C_2$–$C_6$ monoalcohol and/or of a polyol, such as glycerol, butylene glycol, isoprene glycol or propylene glycol.

The surfactants are used in emulsions, in particular, at contents ranging from 0.5 to 30%, preferably from 0.5 to 10%, by weight with respect to the total weight of the emulsion.

The thickening agent can be chosen from modified clays, such as modified magnesium silicate (bentone gel VS38 from Rheox), hectorite modified by distearyldimethylammonium chloride (bentone 38 CE from Rheox), cross-linked poly(acrylic acid)s and guar gums and celluloses which may or may not be modified.

The compositions according to the invention can also comprise colouring materials. These colouring materials can either be inorganic or organic pigments or lakes, which are generally insoluble in aqueous and organic media, or else dyes which are soluble in aqueous or organic media.

The additional pigments must be of a nature and/or used at concentrations which do not mask or only slightly mask the desired soft focus effect. They can be white or coloured, inorganic and/or organic. Mention may be made, among inorganic pigments, of titanium, zirconium or cerium dioxides, as well as zinc, iron or chromium oxides in the form of spherical particles, ferric blue, or pearlescent agents, such as mica covered with titanium oxide, with iron oxide, with natural pigment or with bismuth oxychloride, as well as coloured titanium oxide-coated mica. Mention may be made, among organic pigments, of carbon black and barium, strontium, calcium and aluminium lakes. The pigments can also exhibit a hydrophobic surface or can be treated so as to render their surface hydrophobic; this treatment can be carried out according to methods known to a person skilled in the art; the pigments can in particular be coated with silicone compounds, such as PDMSs, and/or polymers, in particular polyethylenes, and/or amino acids.

These additional pigments are preferably present at levels of less than 15% by weight with respect to the total weight of the composition.

The dyes can be water-soluble dyes, such as the disodium salt of ponceau, the disodium salt of alizarin green, the trisodium salt of amaranth, the disodium salt of tartrazine, the monosodium salt of rhodamine, the disodium salt of fuchsin, xanthophyll, methylene blue or beetroot juice, or alternatively fat-soluble dyes, such as carotene, Sudan red, Sudan brown, D & C Red No. 17, D & C Orange No. 5, D & C Yellow No. 11 or soybean oil.

The dyes are generally present in the compositions at a content of less than 15%, preferably ranging from 0.1 to 10%, by weight with respect to the total weight of the composition.

The composition according to the invention can also comprise a film-forming compound.

The film-forming compound can be chosen from polymers in aqueous dispersion, such as, for example, acrylic, polyester and/or polyurethane polymers in aqueous dispersion. For example, the composition can comprise a stabilized, partially neutralized vinyl acetate/vinyl p-tert-butylbenzoate/crotonic acid copolymer in aqueous dispersion.

The composition according to the invention can also comprise a dispersion of polymer particles in a non-aqueous medium, as disclosed, for example, in the document EP-A-749,747.

The composition according to the invention can additionally comprise any additive normally used in the cosmetics field, such as antioxidants, fragrances, essential oils, preservatives, cosmetic or dermatological active principles, such as moisturizers, vitamins, sphingolipids, such as ceramides, or sunscreen agents, or fat-soluble polymers. Of course, a person skilled in the art will take care to choose this or these optional additional compounds and/or their amount so that the advantageous properties of the composition according to the invention and in particular the soft focus effect are not, or not substantially, detrimentally affected by the envisaged addition. These additives can be present in the composition in a proportion of 0 to 15% by weight.

Another subject-matter of the invention is a process for the non-therapeutic treatment of keratinous substances, in particular a make-up process, which consists in applying a composition as defined above to the said substances, in order to limit, decrease or eliminate the imperfections of these substances and/or to modify the perception of the volume of some regions of the latter.

The invention will be better illustrated using the following example.

EXAMPLE

W/O Foundation Emulsion

| | |
|---|---|
| Mixture of oxyethylenated oxypropylenated polymethylcetyl (dimethyl) (methyl)-siloxane, polyglyceryl-4 isostearate and hexyl laurate, sold under the trade name "Abil WE 09" by the company Goldschmidt | 9 g |
| Acetylated glycol stearate and tristearin mixture, sold under the trade name "Unitwix" by the company Guardian | 0.5 g |
| $D_5$/$D_6$ cyclomethicone | 25 g |
| Diphenyl dimethicone | 6 g |
| Isododecane | 4.55 g |
| Hectorite | 4 g |
| Particulate phase prepared by milling a BEF II plastic sheet sold by the company 3M | 10 g |
| Stabilized, partially neutralized vinyl acetate/vinyl p-tert-butylbenzoate/crotonic acid copolymer in aqueous dispersion | 20 g |
| Diisopropyl adipate | 1 g |
| Water q.s. for | 100 g |

The emulsion is obtained according to the following preparation process:

the pigment is predispersed in a portion of the cyclomethicone;

the remaining oil is homogenized with the surfactants at 40–50° C.;

the mixture is allowed to cool. The pigment and the modified hectorite, the latter having been pre-swollen in a small amount of isododecane, are added to this mixture;

the whole of the aqueous phase is added to the above fatty phase, first with slow stirring and then with very vigorous stirring for 10 minutes;

the copolymer and the diisopropyl adipate are added with slow stirring.

This foundation has a creamy, light and soft texture. Its application to the skin is easy and gives the skin a smooth appearance, masking the imperfections and the wrinkles. The feel is very soft. The comfort is good.

What is claimed is:

1. A method of limiting, decreasing or eliminating blemishes of a keratinous material and/or modifying perception of a volume of regions of said material comprising applying to said material a cosmetic composition comprising a particulate phase comprising particles with a mean dimension of from 5 to 100 microns, said particles comprising at least two consecutive faces having normals at their median point which form, between said normals, an angle at least 90°.

2. The process of claim 1 wherein said angle is in the range of 90° to 175°.

3. The process of claim 1 wherein said particles comprise at least two non-parallel flat consecutive faces.

4. The process according to claim 3 wherein an angle at the vertex separating said two non parallel flat consecutive faces is at most equal to 90°.

5. The process according to claim 4 wherein the angle at the vertex is in the range of 5° to 90°.

6. The process according to claim 1 wherein said particles have a mean dimension ranging from 20 to 50 microns.

7. The process according to claim 1 wherein said particles have a refractive index of greater than 1.

8. The process according to claim 7 wherein said particles have a refractive index in the range of 1.25 to 1.9.

9. The process according to claim 8 wherein said particles have a refractive index in the range of 1.45 to 1.55.

10. The process of claim 1 wherein said particles complise at least one polymer selected from the group consisting of a poly(ethylene terephthalate), a polyethylene, a polypropylene, a polytetrafluoroethylene, a polychlorotetrafluoroethylene, a poly(butylene terephthalate), a polycarbonate, a polyurethane, a polythiourethane, a vinyl, a vinylidene, a styrene, a polyacrylic, a polymethacrylic, a polythioacrylate, a polythiomethacrylate, a transparent silicone, and a copolymer of any mixture thereof.

11. The process according to claim 1 wherein said particles comprise at least one metal oxide selected from the group consisting of an aluminum, an hafnium, a silicon, a titanium, a tungsten, a vanadium, a zinc and a zirconium oxide.

12. The process according to claim 1 wherein said particulate phase is present in said composition in a proportion of 0.5 to 30% by weight of said composition.

13. The process according to claim 12 wherein said proportion is in the range of 2 to 15% by weight of the composition.

14. The process according to claim 1 wherein said composition is in the form of a make-up product selected from the group consisting of a foundation, a face powder, an eye shadow, an eyeliner, a mascara, a concealer and a lipstick.

15. The process of claim 1 wherein said composition is in the form of a emulsion comprising a fatty phase.

16. A process according to claim 15 wherein said fatty phase comprises at least one silicone oil.

17. The process according to claim 16 wherein said at least one silicone oil is a volatile silicone oil.

18. The process according to claim 17 wherein said at least one volatile silicone oil is cyclomethicone.

19. The process according to claim 16 wherein said at least one silicone oil is present in a proportion of at least 5% by weight relative to the total weight of the composition.

20. The process according to claim 16 wherein said at least one silicone oil is present in a proportion of 25% to 95% by weight relative to the total weight of the composition.

21. The process according to claim 15 wherein said fatty phase further comprise a volatile isoparaffin.

22. A cosmetic composition comprising a cosmetically acceptable vehicle and a particulate phase comprising particles with a mean dimension of from 5 to 100 microns, said particles comprising at least two consecutive faces having normals at their median point which form, between said normals, an angle at least 90°.

23. The composition of claim 22 wherein said angle is in the range of 90° to 175°.

24. The composition of claim 22 wherein said particles comprise at least two non-parallel flat consecutive faces.

25. The composition of claim 24 wherein an angle at the vertex separating said two non-parallel flat consecutive faces is at most equal to 90°.

26. The composition of claim 25 wherein the angle at the vertex is in the range of 5° to 90°.

27. The composition of claim 22 wherein said particles have a mean dimension ranging from 20 to 50 microns.

28. The composition of claim 22 wherein said particles have a refractive index of greater than 1.

29. The composition of claim 28 wherein said particles have a refractive index in the range of 1.25 to 1.9.

30. The composition of claim 29 wherein said particles have a refractive index in the range of 1.45 to 1.55.

31. The composition of claim 22 wherein said particles comprise at least one polymer selected from the group consisting of a poly(ethylene terephthalate), a polyethylene, a polypropylene, a polytetrafluoroethylene, a polychlorotetrafluoroethylene, a poly(butylene terephthalate), a polycarbonate, a polyurethane, a polythiourethane, a vinyl, a vinylidene, a styrene, a polyacrylic, a polymethacrylic, a polythioacrylate, a polythiomethacrylate, a transparent silicone, and a copolymer of any mixture thereof.

32. The composition of claim 22 wherein said particles comprise at least one metal oxide selected from the group consisting of an aluminum, an hafnium, a silicon, a titanium, a tungsten, a vanadium, a zinc and a zirconium oxide.

33. The composition of claim 22 wherein said particulate phase is present in said composition in a proportion of 0.5 to 30% by weight of said composition.

34. The composition of claim 33 wherein said proportion is in the range of 2 to 15% by weight of the composition.

35. The composition of claim 34 wherein said composition is in the form of a make-up product selected from the group consisting of a foundation, a face powder, an eye shadow, an eyeliner, a mascara, a concealer and a lipstick.

36. The composition of claim 22 wherein said composition is in the form of a simple emulsion, a complex emulsion, an aqueous gel, an aqueous/alcoholic gel, an anhydrous gel, a serum, a powder, a paste, a solid stick, an aerosol, a foam or a spray.

37. The composition of claim 22 further comprising a fatty phase.

38. A composition of claim 37 wherein said fatty phase comprises at least one silicone oil.

39. The composition according to claim 38 wherein said at least one silicone oil is present in a proportion of at least 5% by weight relative to the total weight of the composition.

40. The composition according to claim 38 wherein said at least one silicone oil is present in a proportion of 25% to 95% by weight relative to the total weight of the composition.

41. The composition of claim 37 wherein said at least one silicone oil is a volatile silicone oil.

42. The composition of claim 41 wherein said at least one volatile silicone oil is cyclomethicone.

43. The composition of claim 22 further comprising at least one non-silicone fatty substance selected from the group consisting of a pasty fatty substance, a gum, a wax and an oil, said substance being of vegetable, mineral, animal or synthetic origin.

44. The composition according to claim 37 further comprising a volatile isoparaffin.

45. The composition of claim 22 further comprising at least one of an aqueous phase, a surface-active agent or a thickening agent.

46. The composition according to claim 22 further comprising a coloring material selected from the group consisting of an inorganic pigment, an organic pigment, a lake and a dye.

47. The composition of claim 22 further comprising at least one additive selected from the group consisting of an antioxidant, a fragrance, an essential oil, a preservative, a cosmetic active principle, a dermatological active principle, a fat-soluble polymer, and a dispersion of polymer particles in an aqueous or nonaqueous medium.

* * * * *